(12) United States Patent
Akita et al.

(10) Patent No.: US 11,229,802 B2
(45) Date of Patent: Jan. 25, 2022

(54) HEART SUPPORT NET AND IMPLANTABLE CARDIOVERTER DEFIBRILLATOR

(71) Applicants: iCorNet Laboratory Co., Ltd., Nagoya (JP); UT-Heart Inc., Tokyo (JP)

(72) Inventors: Toshiaki Akita, Nagoya (JP); Toshiya Sasaki, Nagoya (JP); Jun-ichi Okada, Tokyo (JP); Toshiaki Hisada, Tokyo (JP); Seiryo Sugiura, Tokyo (JP); Takumi Washio, Tokyo (JP)

(73) Assignees: UT-HEART INC., Tokyo (JP); ICORNET LABORATORY CO., LTD., Nagoya (JP)

( * ) Notice: Subject to any disclaimer, the term of this patent is extended or adjusted under 35 U.S.C. 154(b) by 0 days.

(21) Appl. No.: 16/972,568

(22) PCT Filed: Feb. 26, 2019

(86) PCT No.: PCT/JP2019/007381
§ 371 (c)(1),
(2) Date: Dec. 4, 2020

(87) PCT Pub. No.: WO2020/174590
PCT Pub. Date: Sep. 3, 2020

(65) Prior Publication Data
US 2021/0236833 A1 Aug. 5, 2021

(51) Int. Cl.
*A61N 1/39* (2006.01)
*A61N 1/05* (2006.01)

(52) U.S. Cl.
CPC ......... *A61N 1/3956* (2013.01); *A61N 1/0597* (2013.01)

(58) Field of Classification Search
CPC ............................ A61N 1/3956; A61N 1/0597
See application file for complete search history.

(56) References Cited

U.S. PATENT DOCUMENTS

| 4,030,509 A | 6/1977 | Heilman et al. |
| 4,821,723 A | 4/1989 | Baker, Jr. et al. |
| 5,634,938 A | 6/1997 | Swanson et al. |
| 6,076,013 A | 6/2000 | Brennan et al. |

(Continued)

FOREIGN PATENT DOCUMENTS

| JP | S63229069 A | 9/1988 |
| JP | H05337204 A | 12/1993 |

(Continued)

OTHER PUBLICATIONS

Written Opinion of the International Searching Authority (Form PCT/ISA/237) for International Application No. PCT/JP2019/007381 dated May 28, 2019, 6 pages including English translation.

(Continued)

*Primary Examiner* — Eric D. Bertram
(74) *Attorney, Agent, or Firm* — Withrow & Terranova, P.L.L.C.; Vincent K. Gustafson (57) ABSTRACT

A heart support net in one aspect of the present disclosure includes a reception part configured to receive a heart and to be attached to an outer side of a ventricle. The reception part includes: a first conductive part; a second conductive part; and a non-conductive part. The first conductive part and the second conductive part are each knitted into mesh with a conductive yarn. The non-conductive part is knitted into mesh with a non-conductive yarn.

7 Claims, 9 Drawing Sheets

(56) References Cited

U.S. PATENT DOCUMENTS

| | | | |
|---|---|---|---|
| 6,169,922 B1* | 1/2001 | Alferness | A61F 2/2481 |
| | | | 600/16 |
| 6,633,780 B1* | 10/2003 | Berger | A61N 1/0563 |
| | | | 607/119 |
| 6,951,534 B2 | 10/2005 | Girard et al. | |
| 7,163,507 B2 | 1/2007 | Alferness | |
| 7,166,071 B2 | 1/2007 | Alferness | |
| 7,255,674 B2 | 8/2007 | Alferness | |
| 7,276,022 B2 | 10/2007 | Lau et al. | |
| 7,351,200 B2 | 4/2008 | Alferness | |
| 7,587,247 B2 | 9/2009 | Schaer et al. | |
| 7,640,065 B1* | 12/2009 | Kroll | A61N 1/0597 |
| | | | 607/129 |
| 8,801,598 B2 | 8/2014 | Girard et al. | |
| 9,566,443 B2 | 2/2017 | de Canniere | |
| 2002/0103511 A1 | 8/2002 | Alferness et al. | |
| 2003/0199955 A1 | 10/2003 | Struble et al. | |
| 2004/0143154 A1* | 7/2004 | Lau | A61N 1/368 |
| | | | 600/37 |
| 2004/0249242 A1 | 12/2004 | Lau et al. | |
| 2005/0102010 A1 | 5/2005 | Lau et al. | |
| 2005/0283042 A1 | 12/2005 | Meyer et al. | |
| 2007/0197859 A1 | 8/2007 | Schaer et al. | |
| 2009/0156892 A1 | 6/2009 | Lau et al. | |
| 2011/0015478 A1 | 1/2011 | Vanden Hoek et al. | |
| 2013/0184519 A1 | 7/2013 | Alferness et al. | |
| 2015/0018607 A1* | 1/2015 | Akita | D04B 37/02 |
| | | | 600/37 |
| 2015/0148590 A1 | 5/2015 | de Canniere | |
| 2018/0280690 A1 | 10/2018 | Kim et al. | |

FOREIGN PATENT DOCUMENTS

| | | |
|---|---|---|
| JP | 2005329143 A | 12/2005 |
| JP | 2005537871 A | 12/2005 |
| JP | 4261422 B2 | 4/2009 |
| JP | 2009536560 A | 10/2009 |
| JP | 2011056180 A | 3/2011 |
| JP | 2011056182 A | 3/2011 |
| JP | 2016537178 A | 12/2016 |
| JP | 2017025418 A | 2/2017 |
| JP | 2017035395 A | 2/2017 |
| WO | 2004021927 A2 | 3/2004 |

OTHER PUBLICATIONS

English translation of Written Opinion of International Preliminary Examining Authority (Form PCT/IPEA/408) for International Application No. PCT/JP2019/007381 dated Feb. 10, 2020, 4 pages.
English translation of International Preliminary Report on Patentability (Form PCT/IPEA/409) for International Application No. PCT/JP2019/007381 dated Jun. 10, 2020, 7 pages.
International Search Report (Form PCT/ISA/210) for International Application No. PCT/JP2019/007381 dated May 28, 2019, 2 pages, English translation only.
Written Opinion of International Preliminary Examining Authority (Form PCT/IPEA/408) for International Application No. PCT/JP2019/007381 dated Feb. 10, 2020 (8 pages including partial English machine translation of Box V only).
International Preliminary Report on Patentability (Form PCT/IPEA/409) for International Application No. PCT/JP2019/007381 dated Jun. 10, 2020 (7 pages including partial English machine translation of Box V only).
Extended European Search Report for European Patent Application No. 19916564.8, dated Jun. 9, 2021, 8 pages.

* cited by examiner

| BI-PHASIC SHOCK WAVEFORM [ms] | DEFIBRILLATION THRESHOLD [J] |
|---|---|
|  4, 4 | 0.631 |
|  3, 5 | 1.657 |
|  5, 3 | 0.511 |
|  5, 2, 3 | 0.426 |
|  5, 4, 3 | 0.480 |

ND IMPLANTABLE
HEART SUPPORT NET AND IMPLANTABLE CARDIOVERTER DEFIBRILLATOR

TECHNICAL FIELD

The present disclosure relates to a heart support net and an implantable cardioverter defibrillator.

BACKGROUND ART

An implantable cardioverter defibrillator (hereinafter, to be also referred to as ICD) disclosed in patent document 1 below is a medical device to stop a fatal arrhythmia such as ventricular tachycardia or ventricular fibrillation and to recover a cardiac function.

Cited Reference 2 below discloses a technology in which a wire-type electrode conductor is attached with respect to a heart support net that is attached to an outer side of a heart and a defibrillation shock is administered to the heart. The wire-type electrode conductor is interwoven through a mesh of the heart support net in a zigzag manner. Examples of such wire-type electrode conductors include a titanium wire and a platinum coated stainless steel.

PRIOR ART DOCUMENTS

Patent Documents

Patent Document 1: Japanese Unexamined Patent Application Publication No. 2011-056182
Patent Document 2: Specification of U.S. Pat. No. 6,169,922

SUMMARY OF THE INVENTION

Problems to be Solved by the Invention

The current ICD, in many cases, requires electric conduction with high voltage and high energy, and physical burden and mental burden on a patient are large. As such, there has been a demand for an ICD that can effectively operate with a lower energy.

In a technology disclosed in Patent Document 2, as described above, fine metal wires as electrode conductors are interwoven through the mesh of the heart support net. For that reason, a work for interweaving fine metal wires through the mesh requires labor, and a productivity of the heart support net can be declined. For example, if the metal wire is pulled and a part or a whole of the metal wire is withdrawn out of the mesh, it is difficult to return the metal wire to its original position. Thus, in case such a situation occurs, the heart support net cannot but be discarded and a new heart support net has to be used. In order to suppress such a situation from occurring, the heart support net must be carefully and cautiously handled so that the metal wire is not pulled, and therefore a work efficiency in use may be declined.

It is preferable that one aspect of the present disclosure can provide a heart support net that is usable as an electrode of an ICD and is excellent in productivity and work efficiency in use.

Means to Solve the Problems

A heart support net according to one aspect of the present disclosure comprises a reception part configured to receive a heart and to be attached to an outer side of a ventricle. The reception part comprises: a first conductive part; a second conductive part; and a non-conductive part. The first conductive part and the second conductive part are each knitted into mesh with a conductive yarn. The non-conductive part is knitted into mesh with a non-conductive yarn.

According to the heart support net configured in this manner, the heart is introduced inside of the reception part, whereby the reception part can be attached to the outer side of the ventricle. The heart support net may be configured to only contact the heart without generating a touching pressure when a left ventricular end-diastolic pressure (LVEDP) is normal or below normal (10 mmHg or less), to generate a left ventricle surface touching pressure of 5 mmHg or more in a mode of heart failure (LVEDP ≥18 mmHg, heart failure Forrester class IV), and to generate a touching pressure of 10 mmHg when the LVEDP is 30 mmHg. This configuration exhibits a performance of prevention or suppression of a cardiac remodeling without disturbing expansion of the heart in a situation where the LVEDP is low, while preventing or suppressing excessive expansion of the heart in a situation where the LVEDP is high.

The first conductive part and the second conductive part can be coupled to a defibrillator body so as to be used as electrodes, resulting in forming an ICD. The first conductive part and the second conductive part, as described above, each are knitted into mesh with the conductive yarn. Thus, in the heart support net according to the present disclosure, unlike a heart support net, for example, in which metal wires are interwoven through a mesh of a net that is knitted with the non-conductive yarn, it may be possible that withdrawal of a part or a whole of a metal wire out of the mesh of the net is suppressed or avoided. Furthermore, the first conductive part and the second conductive part can be knitted with the conductive yarn using a knitting machine. Thus, it makes unnecessary to further provide a process for interweaving the metal wires through the mesh of the net after a process for knitting the net with the non-conductive yarn, and accordingly a process for manufacturing the heart support net can be simplified and a productivity of the heart support net can be improved.

The conductive yarn may be any electroconductive fiber made from a biocompatible material. The conductive yarn may be, for example, a conductive-resin fine wire in which a metal fine wire such as a tungsten fine wire, a stainless fine wire or a nickel-titanium alloy (nitinol) fine wire, or a conductive-resin fine wire in which a resin material is used as a base material and a conductive filler such as a carbon nano-tube is filled.

The non-conductive yarn may be any non-conductive fiber made from a biocompatible material. The non-conductive yarn may be a yarn made from nonabsorbable single fibers, for example, polyester, polytetrafluoroethylene, foamed polytetrafluoroethylene (foamed PTFE, ePTFE), polypropylene, and poly(difluoromethylene) (hexafluoropropylene-vinylidene fluoride) twisted together. The non-conductive yarn may be a yarn made from absorbable single fibers including, polyglactin, polyglycolic acid, polyethylene glycol, polydioxanone, polylactic acid, polylactide, polyglycolide, polycaprolactone, polyanhydride, polyamide, polyurethane, polyester amide, polyorthoester, polydioxanone, polyacetal, polyketal, polycarbonate, polyorthoester, polyphosphazene, polyhydroxybutyrate, polyhydroxyvalerate, polyalkylene oxalate, polyalkylene succinate, poly (methyl vinyl ether), poly (maleic anhydride), poly (amino acid), and a copolymer, a compound or a mixture thereof twisted together. The non-conductive yarn may be an absorbable thread.

The conductive yarn and/or the non-conductive yarn may be made from a combination of two or more kinds of materials.

The first conductive part, the second conductive part and/or the non-conductive part may be knitted with a combination of two or more kinds of yarns made from different materials.

The non-conductive part may be provided between the first conductive part and the second conductive part.

The first conductive part may correspond to a cardiac base side on an outer side of the ventricle. The second conductive part may correspond to a cardiac apex side on the outer side of the ventricle.

A distance between the first conductive part and the second conductive part may be set in any manner, and may range from 14 mm to 50 mm for a heart with a normal size (for example, height of heart: 90 mm) although the distance depends on a size of the heart.

The first conductive part may correspond to a left ventricle side on the outer side of the ventricle. The second conductive part may correspond to a right ventricle side on the outer side of the ventricle.

The first conductive part may correspond to a front side on the outer side of the ventricle. The second conductive part may correspond to a back side on the outer side of the ventricle.

The first conductive part may correspond to the cardiac base side and the left ventricle side on the outer side of the ventricle. The second conductive part may correspond to the cardiac apex side and the right ventricle side on the outer side of the ventricle.

The first conductive part may correspond to the cardiac base side and the right ventricle side on the outer side of the ventricle. The second conductive part may correspond to the cardiac apex side and the left ventricle side on the outer side of the ventricle.

An implantable cardioverter defibrillator according to another aspect of the present disclosure comprises the above-described heart support net and a defibrillator body. The defibrillator body is coupled to the heart support net.

The defibrillator body may operate to set an electric potential of the first conductive part, which corresponds to the cardiac base side, higher than an electric potential of the second conductive part, which corresponds to the cardiac apex side, and then to set the electric potential of the second conductive part higher than the electric potential of the first conductive part.

EXPLANATION OF REFERENCE NUMERALS

1 . . . ICD, 11, 41, 51, 61, 71 . . . heart support net, 12 . . . defibrillator body, 13 . . . first lead, 14 . . . second lead, 20 . . . reception part, 21 . . . first conductive part, 22 . . . second conductive part, 23 . . . non-conductive part, 24 . . . first opening, 25 . . . second opening.

MODE FOR CARRYING OUT THE INVENTION

Example embodiments of a heart support net and an implantable cardioverter defibrillator according to the present disclosure will be described.

(1) First Embodiment

[Configuration of Heart Support Net and Implantable Cardioverter Defibrillator]

Figure 1A:
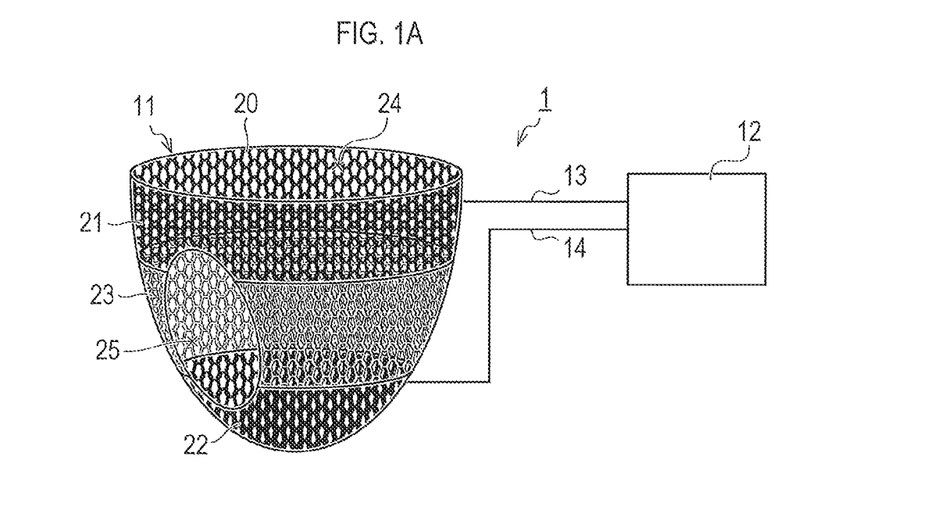
FIG. 1A is a diagram illustrating a schematic configuration of an implantable cardioverter defibrillator and FIG. 1B is a diagram illustrating a schematic configuration of a heart support net.
Figure 1B:
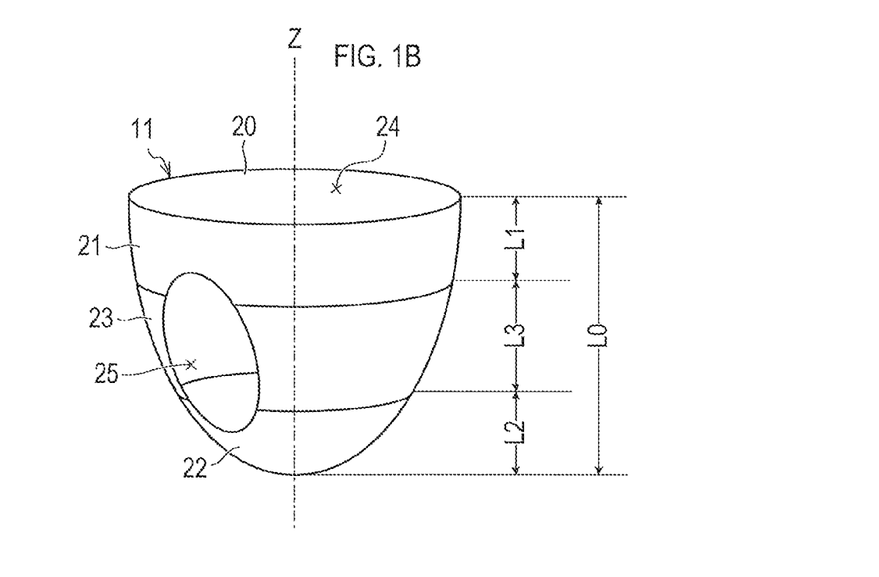

As shown in FIGS. 1A and 1B, an ICD 1 comprises a heart support net 11 and a defibrillator body 12. The defibrillator body 12 and the heart support net 11 are electrically coupled with each other via a first lead 13 and a second lead 14. The heart support net 11 comprises a reception part 20. The reception part 20 is configured to introduce a heart inside of the reception part 20, thereby to be attached to an outer side of a ventricle. The reception part 20 comprises: a first conductive part 21; a second conductive part 22; and a non-conductive part 23. The reception part 20 is further provided with a first opening 24 and a second opening 25.

The first conductive part 21, the second conductive part 22 and the non-conductive part 23 are knitted into mesh by, for example, plain knitting or the like. However, a knitting method is not limited to plain knitting and may be any knitting method that can ensure a desired stretchability. In the present embodiment, the heart support net 1 is configured to only contact the heart without generating a touching pressure when a left ventricular end-diastolic pressure (LVEDP) is normal or below normal (10 mmHg or less), to generate a left ventricle surface touching pressure of 5 mmHg or more in a mode of heart failure (LVEDP ≥18 mmHg, heart failure Forrester class IV), and to generate a touching pressure of 10 mmHg when the LVEDP is 30 mmHg. Owing to this, an effect of prevention or suppression of a cardiac remodeling can be exhibited without disturbing expansion of the heart in a situation where the LVEDP is low, while preventing or suppressing excessive expansion of the heart in a situation where the LVEDP is high.

The first conductive part 21 and the second conductive part 22 are knitted into mesh with a conductive yarn. Any electroconductive fiber made from a biocompatible material is applicable to the conductive yarn. For example, a metal fine wire such as a tungsten fine wire, a stainless fine wire or a nickel-titanium alloy (nitinol) fine wire, or a conductive-resin fine wire in which a resin material is used as a base material and a conductive filler, such as carbon nano-tube is filled may be used as the conductive yarn.

The non-conductive part 23 is knitted into mesh with a non-conductive yarn. Any non-conductive fiber made from a biocompatible material is applicable to the non-conductive yarn. For example, a yarn made from nonabsorbable single fibers such as polyester, polytetrafluoroethylene, foamed polytetrafluoroethylene (foamed PTFE, ePTFE), polypropylene, and poly(difluoromethylene) (hexafluoropropylene-vinylidene fluoride) twisted together may be used as the non-conductive yarn. Also, a yarn made from absorbable single fibers including, polyglactin, polyglycolic acid, polyethylene glycol, polydioxanone, polylactic acid, polylactide, polyglycolide, polycaprolactone, polyanhydride, polyamide, polyurethane, polyester amide, polyorthoester, polydioxanone, polyacetal, polyketal, polycarbonate, polyorthoester, polyphosphazene, polyhydroxybutyrate, polyhydroxyvalerate, polyalkylene oxalate, polyalkylene succinate, poly (methyl vinyl ether), poly (maleic anhydride), poly (amino acid), and a copolymer, a compound or a mixture thereof twisted together may be used as the non-conductive yarn.

The conductive yarn and the non-conductive yarn each may be made from a combination of two or more kinds of materials. The first conductive part 21, the second conductive part 22 and the non-conductive part 23 may be knitted with a combination of two or more kinds of yarns made from different materials. A combined yarn made from a conductive fine wire and a non-conductive fine wire twisted together, as exhibiting a conductivity, is included in the conductive yarn of the present disclosure. With regard to a specific material and thickness of the yarn, any yarn having a property (such as mechanical strength, chemical strength, or stretchability) suitable for an intended use of the heart support net 11 may be used.

The first opening 24 is used to introduce the heart inside of the reception part 20. A circumference of the first opening 24 may be entirely formed with the non-conductive yarn. For example, if it is more convenient with the non-conductive yarn than with the conductive yarn to appress the first opening 24 to a circumference of the heart, an additional non-conductive part may be provided on an opposite side of the non-conductive part 23 having the first conductive part 21 in-between to form the first opening 24 with the added non-conductive part.

The second opening 25 is disposed on an outer side of the right ventricle of the heart that is introduced inside of the reception part 20. Although a shape of the second opening 25 is depicted in an oval shape in FIG. 1A and other drawings for convenience sake, it may be actually in a shape like a chamfered trapezoid. The shape of the second opening 25 is designed in such a manner that an area thereof is slightly smaller than a reference area corresponding to the outer side of the right ventricle and is included in the reference area. Because of this, when the heart support net 11 is attached to the outer side of the ventricle, a part of the reception part 20 situated at a circumference of the second opening 25 is disposed at a position abutting a rim of the aforementioned reference area. At that time, the second opening 25 is disposed slightly closer to the right ventricle than to a border between the right ventricle and the left ventricle (interventricular groove), and disposed slightly closer to the right ventricle than to a border between the right ventricle and a right atrium (atrioventricular groove).

Although not shown in the drawings, the circumference of the second opening 25 may be entirely formed with the non-conductive yarn. In this case, the non-conductive yarn forming the circumference of the second opening 25 may be an absorbable thread. When the circumference of the second opening 25 is formed with the absorbable thread, a part thereof formed with the absorbable thread is absorbed after the lapse of a certain time period after the heart support net 11 is implanted into the heart. Alternatively, the circumference of the second opening 25 is not necessarily provided with the part formed with the non-conductive yarn as described above.

Figure 2A:
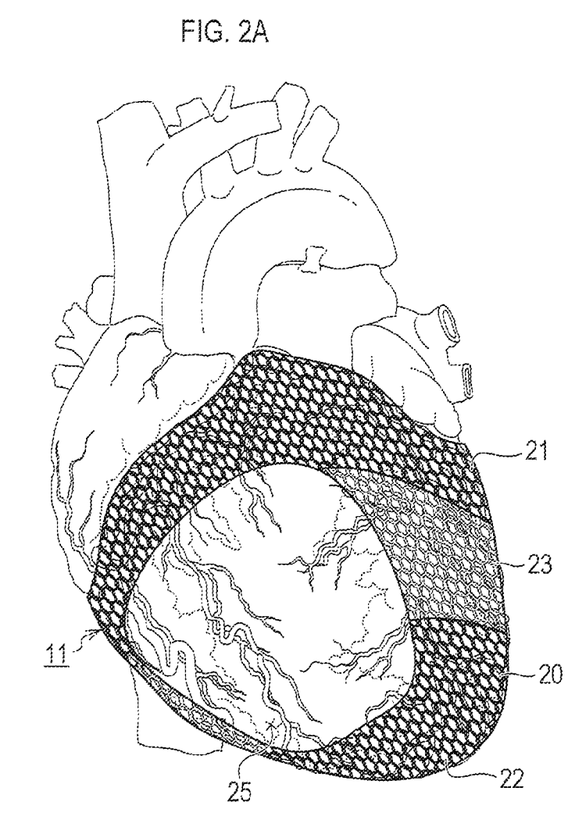
FIG. 2A is a perspective view illustrating a use state of the heart support net in a first embodiment (a state seen from a front side of a heart)
Figure 2B:
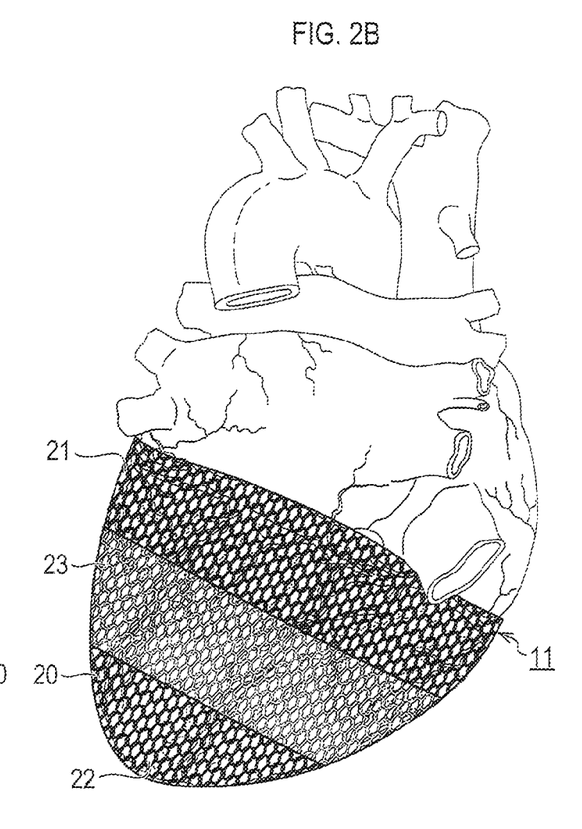
FIG. 2B is a perspective view illustrating a use state of the heart support net in the first embodiment (a state seen from a back side of the heart).

When the heart support net 11 is attached to the heart, the heart is introduced inside of the reception part 20 from a cardiac apex side via the first opening 24. Owing to this, as shown in FIG. 2A and FIG. 2B, the heart support net 11 is attached to the outer side of the ventricle. At that time, the second opening 25 is, as shown in FIG. 2A, disposed on the outer side of the right ventricle. The second opening 25 is provided in this manner, whereby it is possible to make a contact pressure between the heart support net 11 and the heart during a diastole, within an area where the second opening 25 is provided, lower than that within an area where the reception part 20 and the ventricle surface contact with each other.

It is unnecessary to control a shape and/or size of the second opening 25 too strictly, and the shape and/or size may be any shape and/or size as long as the contact pressure applied on the right ventricle side can be reduced. However, if the second opening 25 is excessively small, it is impossible to sufficiently reduce the contact pressure applied to the right ventricle, and thus an appropriate size could be required. On the other hand, if the second opening 25 is excessively large, an attachment position of the heart support net 11 can be likely to deviated to a left ventricle side, and there is a risk that the contact pressure between an outer side of the left ventricle and the support net is declined.

Accordingly, the second opening 25 may be formed in a manner where the outer side of the right ventricle can be sufficiently exposed and the attachment position of the heart support net 11 is not excessively deviated to the left ventricle side. For example, the shape and/or size of the second opening 25 may be set such that a part of the net situated at the circumference of the second opening 25 is in an exact contact with a surrounding of the right ventricle. This configuration enables to inhibit a deviation of the attachment position of the heart support net 11 to the left ventricle during a diastole of the left ventricle, whereby the diastole of left ventricle can be appropriately suppressed.

Meanwhile, the second opening 25 is provided on the outer side of the right ventricle, whereby a contact pressure between the outer side of the right ventricle and the heart support net 11 during a diastole of the heart can be reduced, and thus the diastole on the right ventricle side is not suppressed as much as the left ventricle side and capacity reduction and pressure rise of the right ventricle can be suppressed.

As shown in FIG. 2A and FIG. 2B, the first conductive part 21 corresponds to the cardiac base side on the outer side of the ventricle. The second conductive part 22 corresponds to the cardiac apex side on the outer side of the ventricle. The non-conductive part 23 corresponds to a position closer to the cardiac apex than the first conductive part 21 and closer to the cardiac base than the second conductive part 22 on the outer side of the ventricle. A diameter of the ventricle perpendicular to a direction from the cardiac apex toward the cardiac base (in other words, a direction along a virtual axis Z indicated by a long and two short dashes line in FIG. 1B) is the maximum at a certain position close to the cardiac base. In the first embodiment, a circumference of the certain position is surrounded in a ring-shape by the first conductive part 21.

[Experiment 1]

Figure 3A:
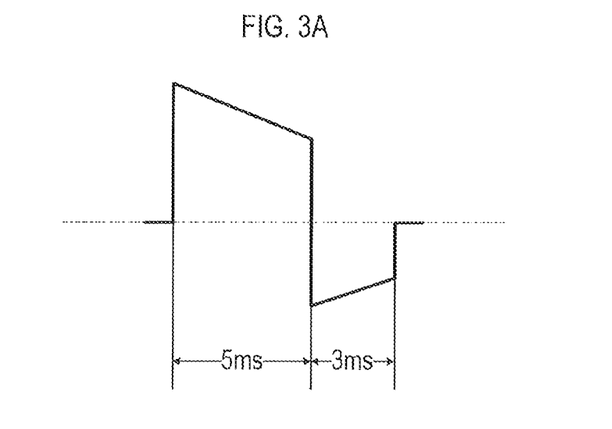
FIG. 3A is a diagram showing a shock waveform of Experiment 1.

Defibrillation analyses were conducted by a computer simulation with use of a mathematical model of a cell. Specifically, a defibrillation success rate was obtained by conducting the defibrillation analyses with a distance between the first conductive part 21 and the second conductive part 22 (the distance corresponding to a length L3 of the non-conductive part 23 along the virtual axis Z shown in FIG. 1B, and hereinafter, to be referred to as a clearance) varied in several ways and a shock energy varied in several ways for each clearance, at 50 shock timings for each. A shock waveform has a shape as shown in FIG. 3A (Bi-Phasic shock). Specifically, from the shock waveform, at first the first conductive part 21 has a high electric potential and the second conductive part 22 has a low electric potential for 5 milliseconds, and then the first conductive part 21 has a low electric potential and the second conductive part 22 has a high electric potential for 3 milliseconds.

Figure 3B:
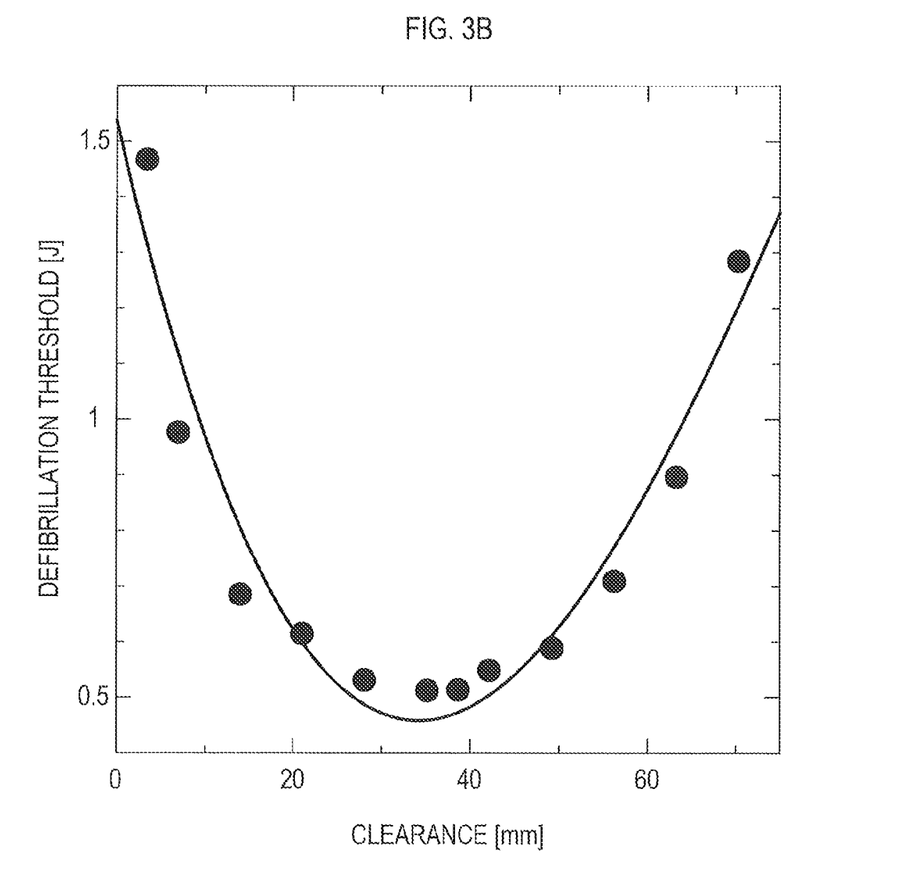
FIG. 3B is a graph showing a relationship between a clearance and a defibrillation threshold in Experiment 1.

For the obtained defibrillation success rate, an approximation was performed by sigmoid functions, and a defibrillation success rate of 50% was defined as a defibrillation threshold. FIG. 3B shows a relationship between the clearance and the defibrillation threshold. As is evident from FIG. 3B, a tendency was confirmed that the defibrillation threshold was high when the clearance was too small and the defibrillation threshold was high even when the clearance was too large, and it was suggested that a minimal value (that is, an optimal value) was located therebetween.

The first conductive part 21 and the second conductive part 22 are likely to have a non-uniform potential gradient between the first conductive part 21 and the second conductive part 22 when the clearance therebetween is too small. It is assumed that, in responding to this, a certain clearance is ensured so that the potential gradient between the first conductive part 21 and the second conductive part 22 becomes more uniform. Also, it is preferable that much of the muscle volume is contained in a current passage running between the first conductive part 21 and the second conductive part 22. It is assumed that, in the first embodiment, a part where the diameter of the ventricle is the maximum is situated at a position closed to the cardiac base, and thus the first conductive part 21 is arranged up to near the maximum diameter of the ventricle, whereby a shock can be delivered without the muscle sticking out over the current passage and an effective defibrillation can be performed.

With a lower defibrillation threshold, the defibrillation success rate increases even if the shock energy is low. In this experiment, when the clearance was set to 35.2 mm (approximately 40% of a height of the ventricle), the defibrillation threshold was the minimum value of 0.511 [J]. In FIG. 1B, a distance L0 is the height of the ventricle. A distance L1 is a height of the first conductive part 21. A distance L2 is a height of the second conductive part 22. A distance L3 is a height of the non-conductive part 23 and the above-described clearance. In this experiment, the distance L0 was set to 90 mm. In this case, the most favorable results were obtained when the distance L1 was set to approximately 25% of the distance L0, the distance L2 was set to approximately 35% of the distance L0, and the distance L3 was set to approximately 40% of the distance L1. When the clearance ranges from 14 mm to 50 mm, the shock energy can be set to less than 0.7[J]. The shock energy of less than 0.7[J] allows a defibrillation at a painless level. Accordingly, with use of the ICD 1 exemplified in the first embodiment, a defibrillation can be performed without imposing an excessive physical burden and mental burden on a patient.

[Experiment 2]

Figure 4:
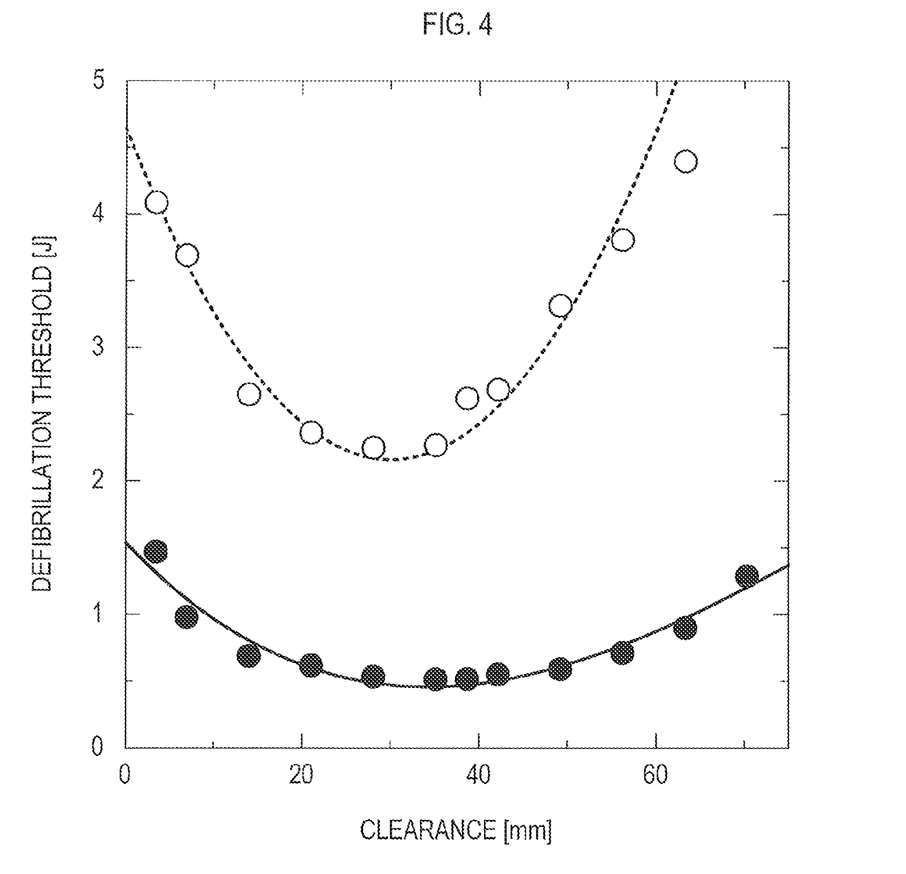
FIG. 4 is a graph showing relationships between the clearance and the defibrillation threshold in Experiment 2.

A defibrillation threshold was obtained by using a same method as the aforementioned Experiment 1, with a shock waveform in which an electric potential was reverse to that in the aforementioned Experiment 1 (that is, a waveform in which at first the first conductive part 21 had a low electric potential and the second conductive part 22 had a high electric potential for 5 milliseconds, and then the first conductive part 21 had a high electric potential and the second conductive part 22 had a low electric potential for 3 milliseconds). FIG. 4 shows a relationship between the clearance and the defibrillation threshold. Results of Experiment 2 are indicated by a broken line in FIG. 4. Results of Experiment 1 are indicated by a solid line in FIG. 4, as well.

It is proven from the results shown in FIG. 4 that the defibrillation threshold is increased by three times or greater when the electric potential is changed in reverse. Accordingly, at least in an electrode arrangement according to the first embodiment, it is considered important, with respect to a Bi-Phasic shock, to set the first conductive part 21 a high electric potential at first, and then to set the second conductive part 22 a high electric potential.

[Experiment 3]

Figure 5:
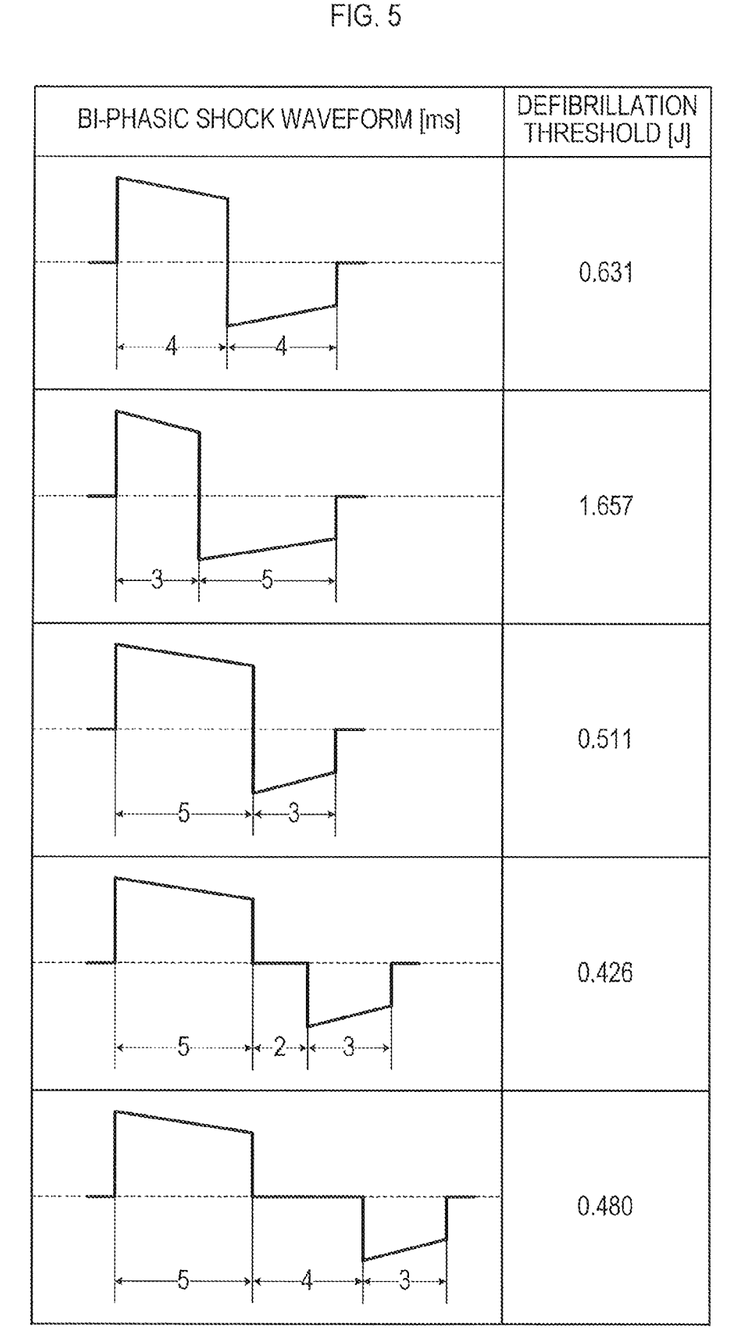
FIG. 5 is a series of diagrams showing relationships between the shock waveforms and the defibrillation thresholds in Experiment 3.

As shown in FIG. 5, a defibrillation threshold was obtained by using the same method as the aforementioned Experiment 1, with a shock waveform changed from the aforementioned Experiment 1. Results are also shown in FIG. 5. The results shown in FIG. 5 indicate that an interval of, for example, approximately 2 milliseconds should be provided between a first shock waveform and a second shock waveform.

[Effects]

As described above, according to the aforementioned heart support net 11, the heart is introduced inside of the reception part 20, whereby the reception part 20 can be attached to the outer side of the ventricle. Owing to this, as described above, a cardiac remodeling can be suppressed. The defibrillator body 12 is coupled to the first conductive part 21 and the second conductive part 22, whereby the first conductive part 21 and the second conductive part 22 are used as electrodes to configure the ICD 1.

Each of the first conductive part 21 and the second conductive part 22 is knitted into mesh with the conductive yarn. Thus, in the heart support net 11, unlike the heart support net, for example, in which the metal wires are interwoven through the mesh of the net that is knitted with the non-conductive yarn, it may be possible that withdrawal of a part or a whole of the metal wires out of the mesh of the net is suppressed or avoided. Furthermore, the first conductive part 21 and the second conductive part 22 can be knitted as intended with the conductive yarn using a knitting machine. Thus, it makes unnecessary to provide a further process for interweaving the metal wire through the mesh of the net after a process for knitting the net with the non-conductive yarn, and accordingly a process for manufacturing the heart support net 11 can be simplified and a productivity of the heart support net 11 can be improved.

According to the aforementioned ICD 1, a defibrillation can be performed at a painless level by suppressing the shock energy to, for example, less than 0.7[J]. Thus, the defibrillation can be performed without imposing an excessive physical burden and mental burden on a patient.

(2) Second Embodiment

Hereinafter, a description will be given of a second embodiment. The second embodiment and the subsequent embodiments each will be described, focusing on differences from the first embodiment in detail. For components similar to those in the first embodiment, a detailed description thereof will not be repeated.

Figure 6A:
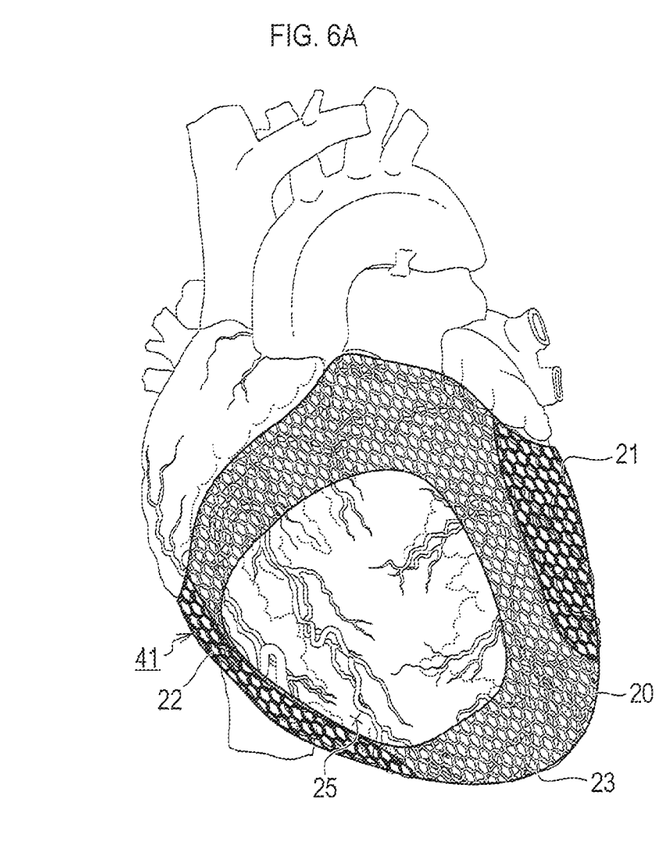
FIG. 6A is a perspective view illustrating a use state of a heart support net in a second embodiment (a state seen from a front side of a heart)
Figure 6B:
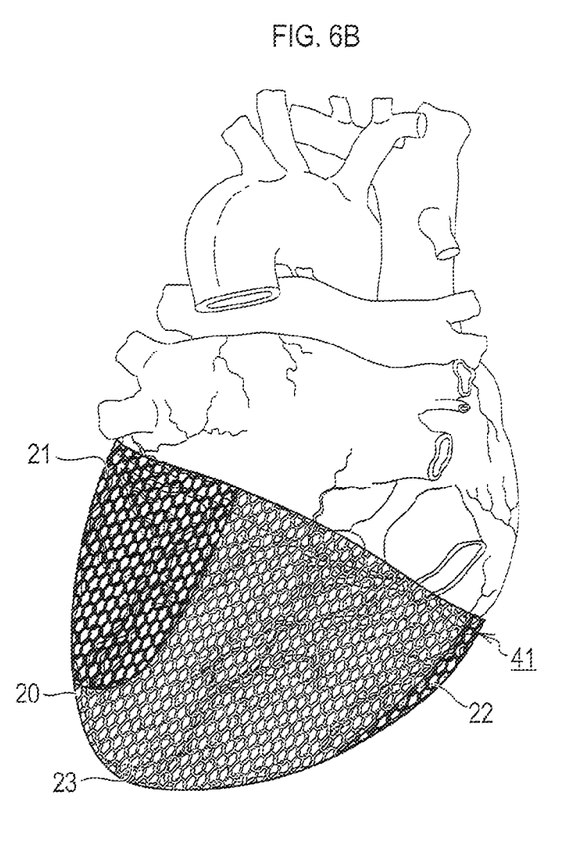
FIG. 6B is a perspective view illustrating a use state of the heart support net in the second embodiment (a state seen from a back side of the heart).

As shown in FIG. 6A and FIG. 6B, a heart support net 41 of the second embodiment differs from the first embodiment in that the first conductive part 21 and the second conductive part 22 are disposed on right and left of a heart in-between. That is to say, the first conductive part 21 corresponds to the left ventricle side on the outer side of the ventricle. The second conductive part 22 corresponds to the right ventricle side on the outer side of the ventricle. The non-conductive part 23 is provided between the first conductive part 21 and the second conductive part 22. The heart support net 41 including the first conductive part 21 and the second conductive part 22 disposed in this manner exhibits a same function and effect as the heart support net 11 of the first embodiment.

(3) Third Embodiment

Hereinafter, a description will be given of a third embodiment.

Figure 7A:
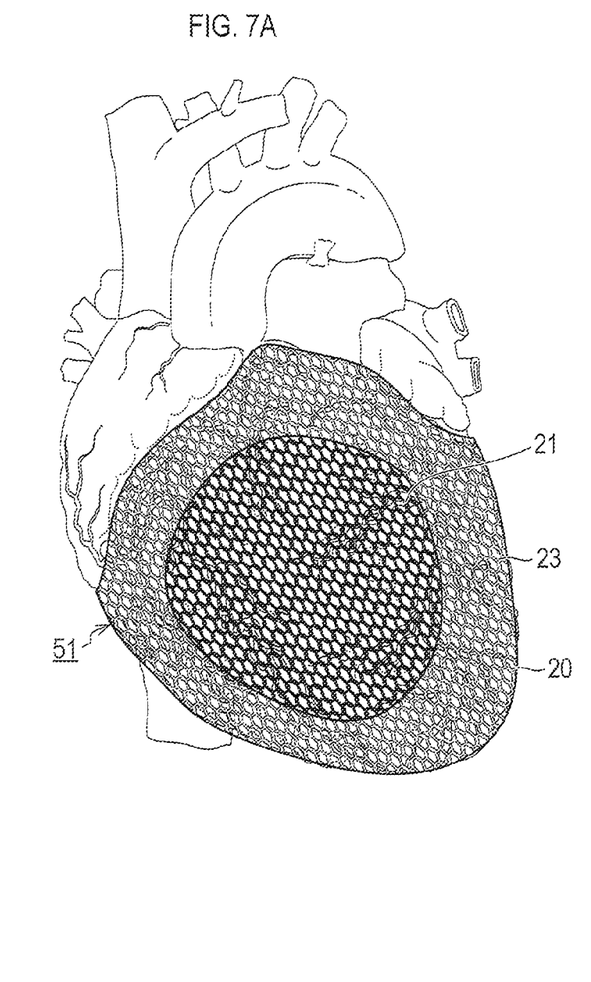
FIG. 7A is a perspective view illustrating a use state of a heart support net in a third embodiment (a state seen from a front side of a heart)
Figure 7B:
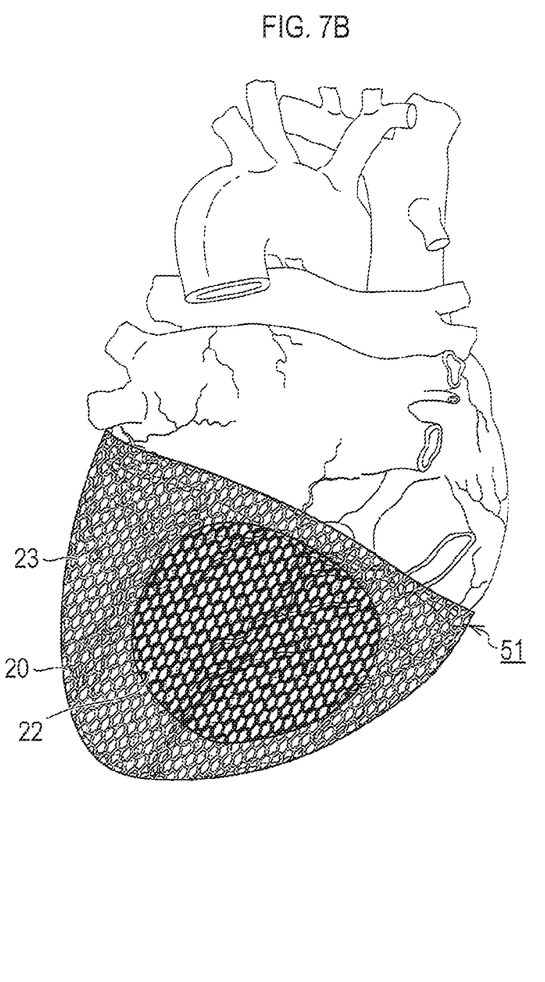
FIG. 7B is a perspective view illustrating a use state of the heart support net in the third embodiment (a state seen from a back side of the heart).

As shown in FIG. 7A and FIG. 7B, a heart support net 51 of the third embodiment differs from the first embodiment in that the first conductive part 21 and the second conductive part 22 are disposed in front and behind a heart in-between. Specifically, the first conductive part 21 corresponds to a front side on the outer side of the ventricle. The second conductive part 22 corresponds to a back side on the outer side of the ventricle. The non-conductive part 23 is provided between the first conductive part 21 and the second conductive part 22. The heart support net 51 including the first conductive part 21 and the second conductive part 22 disposed in this manner exhibits a same function and effect as the heart support net 11 of the first embodiment.

Due to the position where the first conductive part 21 is provided, the second opening 25 is omitted in the heart support net 51 of the third embodiment. In other words, it is an option whether or not to provide the second opening 25. In a case where cardiomegaly is absent, restraint of the left ventricle is unnecessary. Accordingly, in such a case, size and stretchability of the heart support net 51 is optimized so that the restraint of the left ventricle and right ventricle can be reduced without providing the second opening 25. Also, the non-conductive part 23 is knitted with the absorbable thread, whereby the restraint of the left ventricle and right ventricle can be reduced without providing the second opening 25.

(4) Fourth Embodiment

Hereinafter, a description will be given of a fourth embodiment.

Figure 8A:
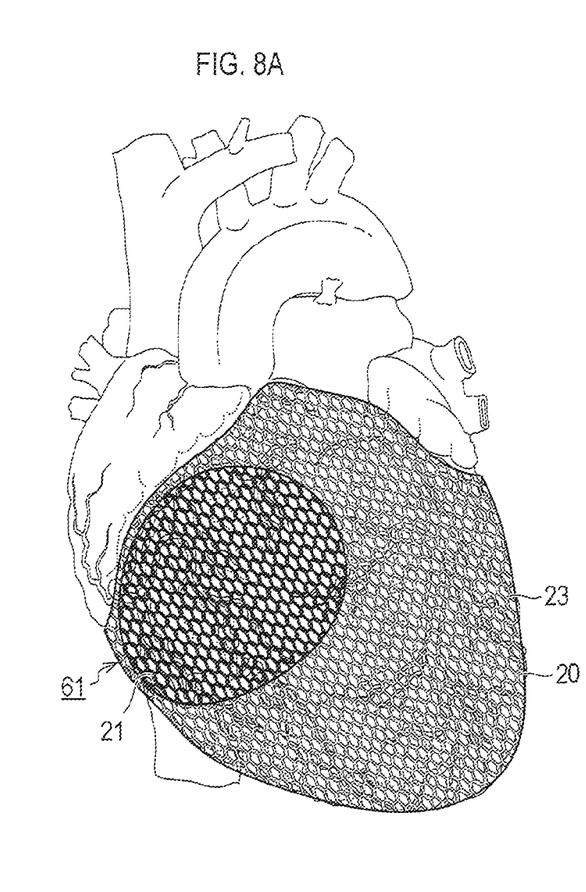
FIG. 8A is a perspective view illustrating a use state of a heart support net in a fourth embodiment (a state seen from a front side of a heart)
Figure 8B:
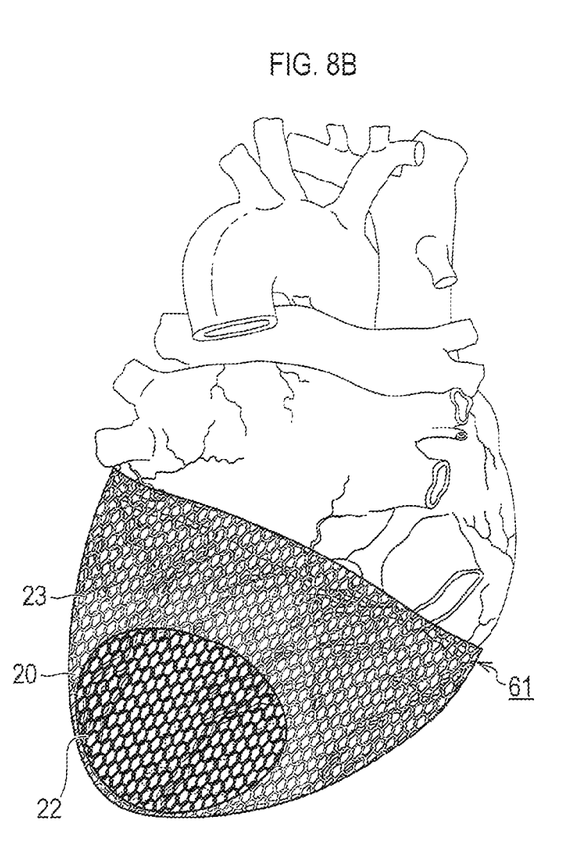
FIG. 8B is a perspective view illustrating a use state of the heart support net in the fourth embodiment (a state seen from a back side of the heart).

As shown in FIG. 8A and FIG. 8B, a heart support net 61 of the fourth embodiment differs from the first embodiment in that the first conductive part 21 and the second conductive part 22 are disposed, as shown in FIG. 8A and FIG. 8B, obliquely upward and obliquely downward of a heart in-between. The first conductive part 21 corresponds to a cardiac base side and a right ventricle side on the outer side of the ventricle. The second conductive part 22 corresponds to a cardiac apex side and a left ventricle side on the outer side of the ventricle. The non-conductive part 23 is disposed between the first conductive part 21 and the second conductive part 22. The heart support net 61 including the first conductive part 21 and the second conductive part 22 disposed in this manner exhibits a same function and effect as the heart support net 11 of the first embodiment. Similarly to the third embodiment, the second opening 25 is omitted in the heart support net 61 of the fourth embodiment.

(5) Fifth Embodiment

Hereinafter, a description will be given of a fifth embodiment.

Figure 9A:
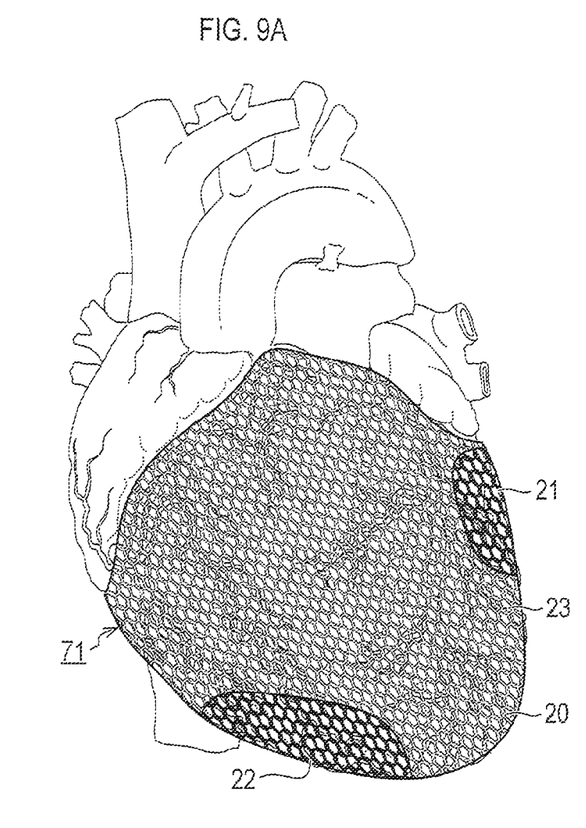
FIG. 9A is a perspective view illustrating a use state of a heart support net in a fifth embodiment (a state seen from a front side of a heart)
Figure 9B:
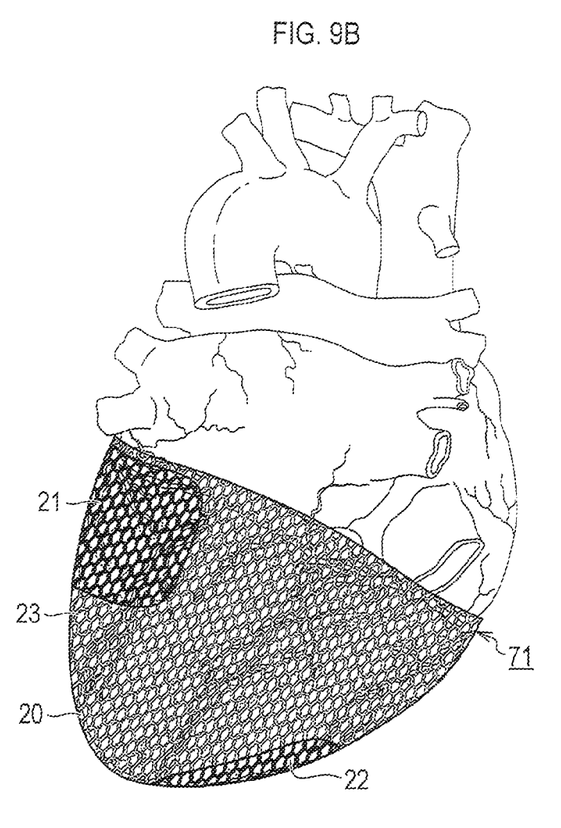
FIG. 9B is a perspective view illustrating a use state of the heart support net in the fifth embodiment (a state seen from a back side of the heart).

As shown in FIG. 9A and FIG. 9B, a heart support net 71 of the fifth embodiment differs from the first embodiment in that the first conductive part 21 and the second conductive part 22 are disposed obliquely upward and obliquely downward of a heart in-between. The first conductive part 21 corresponds to a cardiac base side and a left ventricle side on the outer side of the ventricle. The second conductive part 22 corresponds to a cardiac apex side and a right ventricle side on the outer side of the ventricle. The non-conductive part 23 is disposed between the first conductive part 21 and the second conductive part 22. The heart support net 71 including the first conductive part 21 and the second conductive part 22 disposed in this manner exhibits a same function and effect as the heart support net 11 of the first embodiment. Similarly to the third embodiment, the second opening 25 is omitted in the heart support net 71 of the fifth embodiment.

(6) Other Embodiments

Although the exemplary embodiments of the heart support net and implantable cardioverter defibrillator of the present disclosure have been described, the aforementioned embodiments are given only by way of examples. That is to say, the present disclosure should not be limited by the aforementioned exemplary embodiments, and can be practiced in various manners without departing from the scope of technical ideas of the present disclosure.

For example, when a heart support net is manufactured, a size of a heart may be assumed beforehand to prepare multiple types of heart support net in different sizes. However, a heart support net having a shape and size suitable to a patient may be knitted to be perfectly fitted the heart of the patient by a computer-controlled knitting machine, based on images and results of an electrophysiological examination. The images are photographed by a tomographic device (for example, an MRI). The images show a three-dimensional shape and size of the heart. The heart has an individual difference for each patient. The electrophysiological examination is conducted beforehand. Also, shapes and sizes of the first conductive part 21 and the second conductive part 22, and positions thereof on the heart support net may be optimized for each patient by using a simulation technology, based on the images and the results of the electrophysiological examination as described above. Furthermore, since an optimal electrode arrangement may vary depending on a patient's case, the heart support net 11, 41, 51, 61 shown in the first embodiment to the fourth embodiment may be selectively used to suit the patient's case.

Although the number of each of the provided first conductive part and second conductive part 22 is one in the aforementioned embodiments, at least one of the first conductive part 21 and the second conductive part 22 may be divided into two or more parts and provided in a distributed manner in other embodiments.

Besides the abovementioned, a function achieved by a single component in the aforementioned embodiments may be configured to be achieved by two or more components. A function achieved by two or more components may be configured to be achieved by a single component. A part of the configurations of the aforementioned embodiments may be omitted. At least a part of the configurations of aforementioned embodiments may be added to or replaced with other configurations of another one of the aforementioned embodiments.

The invention claimed is:

1. A heart support net comprising:
a reception part configured to receive a heart and to be attached to an outer side of a ventricle, the reception part comprising:
  a first conductive part and a second conductive part each knitted into mesh with a conductive yarn; and
  a non-conductive part knitted into mesh with a non-conductive yarn,
  the non-conductive part being disposed between the first conductive part and the second conductive part,
  the first conductive part corresponding to a cardiac base side on the outer side of the ventricle,
  the second conductive part corresponding to a cardiac apex side on the outer side of the ventricle,
  the first conductive part having a maximum height of approximately 25% of a height of the ventricle,
  the second conductive part having a maximum height of approximately 35% of the height of the ventricle, and
  the non-conductive part having a maximum height of approximately 40% of the height of the ventricle.

2. The heart support net according to claim 1, wherein a distance between the first conductive part and the second conductive part ranges from 14 mm to 50 mm.

3. A heart support net comprising:
a reception part configured to receive a heart and to be attached to an outer side of a ventricle, the reception part comprising:
a first conductive part and a second conductive part each knitted into mesh with a conductive yarn; and
a non-conductive part knitted into mesh with a non-conductive yarn,
the non-conductive part being disposed between the first conductive part and the second conductive part,
the first conductive part corresponding to a cardiac base side on the outer side of the ventricle,
the second conductive part corresponding to a cardiac apex side on the outer side of the ventricle,
the first conductive part having a height of approximately 25% of a height of the ventricle,
the second conductive part having a height of approximately 35% of the height of the ventricle, and
the non-conductive part having a height of approximately 40% of the height of the ventricle,
wherein the heart support net is configured to only contact the heart without generating a touching pressure when a left ventricular end-diastolic pressure (LVEDP) is 10 mmHg or less, to generate a left ventricle surface touching pressure of 5 mmHg or more in a mode of heart failure wherein LVEDP ≥18 mmHg and classified as heart failure Forrester class IV, and to generate a touching pressure of 10 mmHg when the LVEDP is 30 mmHg.

4. An implantable cardioverter defibrillator comprising:
a heart support net comprising a reception part configured to receive a heart and to be attached to an outer side of a ventricle, the reception part comprising:
  a first conductive part and a second conductive part each knitted into mesh with a conductive yarn; and
  a non-conductive part knitted into mesh with a non-conductive yarn,
  the non-conductive part being disposed between the first conductive part and the second conductive part,
  the first conductive part corresponding to a cardiac base side on the outer side of the ventricle,
  the second conductive part corresponding to a cardiac apex side on the outer side of the ventricle,
  the first conductive part having a maximum height of approximately 25% of a height of the ventricle,
  the second conductive part having a maximum height of approximately 35% of the height of the ventricle, and
  the non-conductive part having a maximum height of approximately 40% of the height of the ventricle; and
a defibrillator body configured to be coupled to the heart support net.

5. The implantable cardioverter defibrillator according to claim 4, wherein a distance between the first conductive part and the second conductive part ranges from 14 mm to 50 mm.

6. The implantable cardioverter defibrillator according to claim 4, wherein the defibrillator body is configured to set an electric potential of the first conductive part higher than an electric potential of the second conductive part, and then to set the electric potential of the second conductive part higher than the electric potential of the first conductive part.

7. An implantable cardioverter defibrillator comprising:
a heart support net comprising a reception part configured to receive a heart and to be attached to an outer side of a ventricle, the reception part comprising:
  a first conductive part and a second conductive part each knitted into mesh with a conductive yarn; and
  a non-conductive part knitted into mesh with a non-conductive yarn,
  the non-conductive part being disposed between the first conductive part and the second conductive part,
  the first conductive part corresponding to a cardiac base side on the outer side of the ventricle,
  the second conductive part corresponding to a cardiac apex side on the outer side of the ventricle,
  the first conductive part having a height of approximately 25% of a height of the ventricle,
  the second conductive part having a height of approximately 35% of the height of the ventricle, and
  the non-conductive part having a height of approximately 40% of the height of the ventricle; and
a defibrillator body configured to be coupled to the heart support net,
  wherein the heart support net is configured to only contact the heart without generating a touching pressure when a left ventricular end-diastolic pressure (LVEDP) is 10 mmHg or less, to generate a left ventricle surface touching pressure of 5 mmHg or more in a mode of heart failure wherein LVEDP ≥18 mmHg and classified as heart failure Forrester class IV, and to generate a touching pressure of 10 mmHg when the LVEDP is 30 mmHg.

* * * * *